United States Patent
Eder et al.

(10) Patent No.: US 10,065,004 B2
(45) Date of Patent: Sep. 4, 2018

(54) MEDICAL OR DENTAL DEVICE FOR DISPENSING A POWDERED MEDIUM

(71) Applicant: W&H Dentalwerk Bürmoos GmbH, Bürmoos (AT)

(72) Inventors: Karlheinz Eder, Michaelbeuern (AT); Wolfgang Perwein, Lamprechtshausen (AT); Josef Spitzauer, Loipferding (AT); Udo Hoermann, Oberalm (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 58 days.

(21) Appl. No.: 15/336,709

(22) Filed: Oct. 27, 2016

(65) Prior Publication Data
US 2017/0119980 A1    May 4, 2017

(30) Foreign Application Priority Data
Oct. 29, 2015    (EP) .................................... 15192001

(51) Int. Cl.
| A61C 3/02 | (2006.01) |
| A61M 13/00 | (2006.01) |
| A61C 3/025 | (2006.01) |

(52) U.S. Cl.
CPC ............. A61M 13/00 (2013.01); A61C 3/025 (2013.01); *A61M 2202/064* (2013.01)

(58) Field of Classification Search
CPC .. A61C 3/025; A61M 13/00; A61M 2202/064
See application file for complete search history.

(56) References Cited

U.S. PATENT DOCUMENTS

| 2,950,564 A | 8/1960 | Bonine |
| 3,815,286 A | 6/1974 | Piet |

(Continued)

FOREIGN PATENT DOCUMENTS

| DE | 60308914 | 12/2006 |
| JP | S59156341 | 9/1984 |

(Continued)

OTHER PUBLICATIONS

Search Report for European Application No. 15192001 (dated Dec. 16, 2015).

*Primary Examiner* — Heidi M Eide
(74) *Attorney, Agent, or Firm* — Klarquist Sparkman, LLP (57) ABSTRACT

A medical or dental device for dispensing a powdered medium with a container having a container interior space. The container can be connected to a compressed gas source to convey the powdered medium together with the compressed gas out of the interior space, and to a dispensing unit, so that the powdered medium is conveyed with the compressed gas to the dispensing unit. The container comprises: a wall, and a bottom that is connected to the wall and has at least one bore through which compressed gas from the compressed gas source can be conducted into the interior space. A swirl plate made of a porous material is provided at the bottom. Compressed gas can be conducted through the porous swirl plate into the interior space to aerate at least a portion of the powdered medium without conveying the powdered medium out of the interior space to the dispensing unit.

40 Claims, 2 Drawing Sheets

(56) References Cited

U.S. PATENT DOCUMENTS

| | | | | |
|---|---|---|---|---|
| 4,494,932 A * | 1/1985 | Rzewinski | ............ | A61C 3/025 433/88 |
| 2005/0267628 A1 | 12/2005 | Crowder et al. | | |
| 2007/0175476 A1 | 8/2007 | Lipowicz | | |
| 2009/0246730 A1 * | 10/2009 | Takamori | ............... | A61C 3/025 433/88 |
| 2011/0223555 A1 * | 9/2011 | Thoms | ................... | A61C 3/025 433/29 |
| 2014/0014104 A1 | 1/2014 | Hoekman et al. | | |

FOREIGN PATENT DOCUMENTS

| WO | WO02/056948 | 7/2002 |
|---|---|---|
| WO | WO2007/014246 | 2/2007 |

* cited by examiner

MEDICAL OR DENTAL DEVICE FOR DISPENSING A POWDERED MEDIUM

CROSS REFERENCE TO RELATED APPLICATION

The present application claims priority from pending European Patent Application No. 15192001.4, filed Oct. 29, 2015, which is incorporated herein by reference.

BACKGROUND

Field

The present invention relates to a medical or dental device for dispensing a powdered medium that is fluidized by a compressed gas onto human or animal tissue or a tissue replacement material.

Description of Prior Art

Such a device is known from patent application WO 2007/014246 A2. The device for dispensing a powdered medium can be connected to a dental unit for supplying it with compressed gas and water and it includes a container for storing the powdered medium and a dispensing unit in the form of a handpiece with a nozzle through which the powdered medium together with the compressed gas can be dispensed to a treatment site. Compressed gas is supplied to the container and to the powder contained in it in order to convey the powdered medium out of the container and to the dispensing unit.

In practice, it is difficult to operate such a device with constant operating parameters. Thus it is often observed that the amount of powdered medium conveyed by the compressed gas out of the container to the dispensing unit varies greatly, for example, as a function of the filling level of the powdered medium in the container or as a function of the type of powdered medium, for example, its grain size. Since the powdered medium stored in the container is very fine, i.e., has small grain sizes and is often hygroscropic, it additionally frequently occurs that the powdered medium forms lumps in the container which also results in considerable variations in the amount of powdered medium conveyed through the compressed gas.

SUMMARY

Based on the foregoing it would be advantageous to create a medical or dental device for dispensing a powdered medium having a more constant operation, in particular having less variation in the load of powdered medium in the compressed gas, and in which the formation of lumps of the powdered medium in the container will have less effect on the conveyance of the powdered medium to the dispensing unit in comparison with current practice.

According to an embodiment a medical or dental device for dispensing a powdered medium onto human or animal tissue or onto a tissue replacement material comprises a container for storing the powdered medium in a container interior space, wherein the container can be connected to a compressed gas source and compressed gas from the compressed gas source can be conducted into the container interior space in order to convey the powdered medium with the compressed gas out of the container interior space. The container can be connected to a dispensing unit so that the powdered medium with the compressed gas is conveyed to the dispensing unit and can be dispensed by the dispensing unit in the direction of the human or animal tissue or the tissue replacement material. The container comprises a container wall, which defines at least a portion of the container interior space and a container bottom connected to the container wall and having at least one bore through which compressed gas can be sent from the compressed gas source into the container interior space. In addition, a swirl plate of porous material which is permeable for compressed gas is provided at the container bottom, so that compressed gas can be sent through this porous material and into the container interior space in order to loosen up or aerate at least a portion of the powdered medium in the container interior space without conveying the powdered medium out of the container interior space to the dispensing unit.

Providing a swirl plate made of a porous material that is permeable for compressed gas and through which compressed gas can be passed into the container interior space causes a loosening, aerating and/or hovering of the powdered medium in the container interior space. Alternatively, the effect of the compressed gas blown through the porous material can thus be described as the compressed gas inducing the powdered medium into a fluid-like state or an active motion state, i.e., a fluidized state. This loosening, aerating or fluidization permits a uniform charging of the compressed gas with the powdered medium and also counteracts the formation of lumps of powdered medium and/or separates particles of the powdered medium that are lumped together from one another. The medical or dental device can thus be operated with substantially more constant operating parameters.

The compressed gas used is preferably compressed air which is received by the medical or dental device for dispensing a powdered medium from a compressed air source, for example, a compressor. The medical or dental device for dispensing a powdered medium is therefore connected to the compressed air source via a compressed gas line/compressed air line.

As will be described in detail further below, the container preferably comprises a standpipe which extends into the container interior space and which has at least one suction or intake opening for intake of powdered medium stored in the container to convey the powdered medium through the standpipe to the dispensing unit. The at least one suction or intake opening and the swirl plate that is permeable for compressed gas are preferably arranged close to one another or adjacent to one another, so that the loosening, aeration or fluidization of the powdered medium takes place in particular in a volume at the at least one intake opening so that the intake of powdered medium into the standpipe is additionally favored.

Preferably, all of the powdered medium stored in the container is loosened, aerated or fluidized by the compressed gas which passes through the porous material of the compressed-gas-permeable swirl plate and into the container interior space.

The compressed-gas-permeable swirl plate is preferably made of glass, metal or plastic. The compressed-gas-permeable swirl plate is preferably designed as a cylindrical disk. The compressed-gas-permeable swirl plate preferably has a top side facing the container interior space, a bottom side remote from the container interior space and a body with a lateral surface extending between the top side and the bottom side. The compressed-gas-permeable swirl plate, in particular its body, preferably comprises a plurality of channels or pores which in particular connect the top side and the bottom side and open into openings on the top side and the bottom side so that the compressed-gas-permeable swirl plate is permeable for compressed gas. The diameter or the size of the channels or pores is preferably equal to or less than 20 µm, in particular equal to or less than 14 µm, so that particles of the powdered medium essentially cannot enter the pores or channels or pass through them.

The compressed-gas-permeable swirl plate is preferably designed, in particular because of the plurality of its channels or pores, so that the compressed gas supplied to the compressed-gas-permeable swirl plate emerges at least over most of its top side, so that in particular the aerating or fluidization of the powdered medium is accomplished without conveying the powdered medium to the dispensing unit from the container interior space.

The container interior space preferably includes at least one section or partial volume which tapers in the direction of the container bottom. The compressed-gas-permeable swirl plate is especially preferably arranged in or on the section of the container interior space that tapers in the direction of the container bottom. The at least one intake opening of the standpipe is especially preferably arranged in the section of the container interior space that tapers in the direction of the container bottom. These features advantageously and in particular in combination produce a reliable flow of the powdered medium in the container interior space, a reliable intake through the intake openings of the standpipe and/or counteract development of a bridge in the powdered medium.

The compressed-gas-permeable swirl plate preferably forms an intermediate bottom which delimits the container interior space and separates the container interior space from the container bottom. This advantageously ensures that the powdered medium will be deposited exclusively on the compressed-gas-permeable swirl plate (and not directly on the container bottom) and will thus be reliably loosened, aerated or fluidized.

Preferably, below the compressed-gas-permeable swirl plate, in particular between the compressed-gas-permeable swirl plate and the container bottom, there is provided a compressed gas chamber for supplying compressed gas over a large surface area of the compressed-gas-permeable swirl plate, wherein said compressed gas chamber extends directly along the bottom side of the compressed-gas-permeable swirl plate, preferably over a large planar surface area of it. The compressed gas chamber preferably extends over at least 50%, in particular preferably over at least 75% of the bottom side of the compressed-gas-permeable swirl plate. The compressed gas chamber is preferably designed as an annular chamber beneath the disk-shaped compressed-gas-permeable swirl plate.

The compressed-gas-permeable swirl plate is preferably arranged at a distance from the container bottom through a shoulder or a spacer, wherein the compressed gas chamber comprises in particular the distance produced by the shoulder or the spacer.

A compressed gas line which is identified below as the first compressed gas line for (exclusive) supply of compressed gas to the porous material of the compressed-gas-permeable swirl plate preferably opens into the compressed gas chamber. The compressed gas chamber is preferably designed and provided to receive the compressed gas supplied by the compressed gas line and in particular to distribute it over a large (planar) surface area of the bottom side of the compressed-gas-permeable swirl plate, so that the compressed gas enters the porous material of the compressed-gas-permeable swirl plate at a number of locations on the bottom side.

The compressed-gas-permeable swirl plate preferably comprises a bore, which in particular is arranged centrally in the compressed-gas-permeable swirl plate, so that the compressed gas from the compressed gas source can be conducted through this bore into the container interior space to convey the powdered medium out of the container interior space. In particular the bore thus forms a portion of a line or accommodates a line, which conducts the compressed gas directly into the container interior space without the compressed gas having to flow through the channels or pores of the compressed-gas-permeable swirl plate. The bore preferably has a diameter of several millimeters.

The medical or dental device, in particular the container preferably comprises a first compressed gas line and a second compressed gas line. The first compressed gas line is supplied with compressed gas to supply (exclusively) the porous material of the compressed-gas-permeable swirl plate, preferably via the compressed gas chamber extending along the bottom side of the compressed-gas-permeable swirl plate, so that the compressed gas conveyed through the first compressed gas line passes (exclusively) through the porous material of the compressed-gas-permeable swirl plate into the container interior space of the container, to loosen or aerate at least a portion of the powdered medium in the container interior space. The second compressed gas line is provided for conducting compressed gas (exclusively) directly into the container interior space for conveying the powdered medium with the compressed gas out of the container interior space. The compressed gas conveyed in the second compressed gas line thus flows in particular not through the pores and channels of the porous material of the compressed-gas-permeable swirl plate. The compressed gas conveyed in the second compressed gas line flows especially preferably through the second compressed gas line directly, in particular through the bore in the compressed-gas-permeable swirl plate, into the container interior space or into the standpipe.

The first compressed gas line and the second compressed gas line are designed as separate compressed gas lines. Due to the fact that the two separate compressed gas lines are provided, it is advantageously possible to convey compressed gas with different parameters to the compressed-gas-permeable swirl plate and directly into the container interior space, for example, different compressed gas volume flows.

At least the first compressed gas line or the second compressed gas line preferably includes a throttle element, for example, a throttle valve to be able to adjust the compressed gas volume flow flowing through the first compressed gas line or the second compressed gas line. The first compressed gas line especially preferably comprises a first throttle element and the second compressed gas line comprises a second throttle element. The at least one throttle element or the first throttle element and the second throttle element is/are preferably designed so that the compressed gas volume flow in the first compressed gas line and in the second compressed gas line are different after passing through the throttle element(s), in particular such that the compressed gas volume flow in the first compressed gas line (to supply the compressed-gas-permeable swirl plate) is greater than that in the second compressed gas line. In several practical experiments, a particularly good and constant operating behavior of the medical or dental device was thus achieved, in particular a uniform loading of the compressed gas with powdered medium.

The second compressed gas line preferably extends through the bore of the compressed-gas-permeable swirl plate or this bore is part of the second compressed gas line. This creates a particularly space-saving design.

Preferably, the bore of the compressed-gas-permeable swirl plate and/or the compressed-gas-permeable swirl plate and/or at least a section of the second compressed gas line and/or at least a section of the container interior space and/or at least a section of the container wall is/are arranged concentrically, in particular around a central axis of the container.

The first compressed gas line and the second compressed gas line can preferably be connected to a common compressed gas source, in particular through a common compressed gas supply line. The common compressed gas supply line can especially preferably be connected to a dental unit with a patient's chair so that the medical or dental device can be supplied with compressed gas via or through the dental unit.

The first compressed gas line and the second compressed gas line are preferably arranged in a supply block that can be connected to the container. The supply block is preferably designed as a connecting element or an attachment element between the container and a base part or an operating part of the medical or dental device. The supply block preferably releasably or permanently connects the container to the base part or the operating part. The supply block is preferably made of metal, wherein the first compressed gas line and the second compressed gas line are designed as bores in the supply block.

An extension of the supply block in which a section of the second compressed gas line is preferably arranged, protrudes into the bore of the compressed-gas-permeable swirl plate, thus resulting in a fixation and alignment of the compressed-gas-permeable swirl plate, the supply block and the container relative to one another advantageously. The diameter or width of the extension of the supply block is preferably smaller than the diameter or width of another section of the supply block. Preferably only a section of the second compressed gas line is arranged in the extension of the supply block, whereas in the additional section of the supply block, there is arranged a section of the first compressed gas line and the second compressed gas line.

At least one sealing element is preferably provided at the interface between the supply block, in particular its extension, and the compressed-gas-permeable swirl plate and/or the compressed gas chamber and/or the container, in particular the container bottom, to prevent the flow of compressed gas along the interface.

The medical or dental device, in particular the container, preferably includes a standpipe having a first end and a second end, wherein the standpipe extends into the container interior space. The first end of the standpipe is connected to the second compressed gas line and/or to the extension of the supply block and/or protrudes into the bore in the compressed-gas-permeable swirl plate, so that compressed gas can flow out of the second compressed gas line into the standpipe (and thus directly into the container interior space). The standpipe additionally has at least one intake or suction opening, preferably a plurality of intake openings, for intake or suction of powdered medium stored in the container, so that powdered medium is drawn through the at least one intake opening into the standpipe by the compressed gas supplied by the second compressed gas line (in particular via the Venturi effect) and is conveyed with the compressed gas through the standpipe in the direction of the second end.

The inside diameter of the standpipe preferably expands from the at least one intake opening in the direction of the second end. Preferably, three or more intake openings are provided which are arranged around the circumference of the standpipe, preferably uniformly around the circumference of the standpipe.

The at least one suction or intake opening is preferably arranged at the first end of the standpipe, in particular close to the compressed-gas-permeable swirl plate. Thus the at least one intake opening is provided in a partial volume of the container interior space, in which the loosening, aeration or fluidization of the powdered medium is particularly intense, so that a particularly good and constant operating behavior of the medical or dental device, in particular a constant loading of the compressed gas with the powdered medium, is achieved.

The medical or dental device, in particular the container preferably includes a non-return valve, which is designed to prevent powdered medium from the container interior space from entering the second compressed gas line. The non-return valve includes, for example, a duckbill valve.

At least a part of the non-return valve is preferably arranged in the second compressed gas line, in particular in the supply block or in the extension of the supply block. The non-return valve preferably passes through the bore in the compressed-gas-permeable swirl plate. Preferably at least a part of the non-return valve protrudes into the standpipe.

The non-return valve is preferably operable by the compressed gas that can be conveyed in the second compressed gas line such that the non-return valve opens when the gas pressure of the compressed flowing in the second compressed gas line exceeds a predetermined value and closes when the gas pressure of the compressed gas flowing in the second compressed gas line drops below a predetermined value.

The container, in particular the container wall, preferably comprises an opening, through which the compressed gas loaded with the powdered medium can be conveyed out of the container and in the direction of the dispensing unit. The opening is preferably connected to a conveying tube and/or the conveying tube is accommodated in the opening, wherein the conveying tube is designed to convey the compressed gas loaded with the powdered medium in the direction of the dispensing unit. The opening or the conveying tube is preferably fluidly connected to the standpipe. The inside diameter of the conveying tube is preferably smaller than the inside diameter of the standpipe. The conveying tube is preferably connected to a line which conveys the compressed gas loaded with the powdered medium in the direction of the dispensing unit. This line preferably extends up to or into the dispensing unit.

The medical or dental device preferably also comprises at least one of the following elements: a dispensing unit, in particular a handle having a nozzle device, which is designed for dispensing the powdered medium in the direction of the human or animal tissue or the tissue replacement material; a liquid line for conducting a liquid in the direction of the dispensing unit, so that the liquid can be dispensed through the dispensing unit in the direction of the human or animal tissue or the tissue replacement material; a base part or an operating part, in which, for example, at least a section of the first compressed gas line and/or the second compressed gas line and/or the common compressed gas supply line and/or a moisture separator for separating moisture from the compressed gas that is supplied to the container and/or at least a section of the liquid line and/or at least one control element for controlling the throttle element for the compressed gas and/or at least one control element for controlling the liquid flow-through rate through the liquid line and/or the supply block and/or a receptacle for the container are provided; a first supply tubing having a compressed gas line for conducting compressed gas from a compressed gas source to the base part or operating part or to the container and preferably having a liquid line for conducting liquid from a liquid source in the direction of the dispensing unit; a second supply tubing with a compressed gas line for conducting the compressed gas loaded with the powdered medium from the base part or the operating part or the container in the direction of the dispensing unit and preferably having a liquid line for conducting a liquid in the direction of the dispensing unit; a compressed gas source.

A method for operating a medical or dental device for dispensing a powdered medium onto human or animal tissue or onto a tissue replacement material is described below, wherein the medical or dental device comprises a container for storing the powdered medium in a container interior space. The container can be connected to a compressed gas source and compressed gas of the compressed gas source can be conducted into the container interior space to convey the powdered medium with the compressed gas out of the container interior space. The container of the medical or dental device can also be connected to a dispensing unit, so that the powdered medium is conveyed with the compressed gas to the dispensing unit and can be dispensed by the dispensing unit in the direction of the human or animal tissue or the tissue replacement material. The container has in particular a container wall, which defines at least a portion of the container interior space and a container bottom connected to the container wall and having at least one bore, wherein compressed gas from the compressed gas source can be conducted through the bore into the container interior space. A compressed-gas-permeable swirl plate made of a porous material is provided at the container bottom. The method includes the step, that compressed gas is conducted through the porous material of the compressed-gas-permeable swirl plate into the container interior space to loosen, aerate or fluidize at least a portion of the powdered medium in the container interior space without conveying the powdered medium out of the container interior space to the dispensing unit.

Preferably in this method, compressed gas is additionally conducted through the standpipe described already above to draw the powdered medium into the standpipe, preferably by means of a Venturi effect, and in particular to convey it through the standpipe to the dispensing unit.

The standpipe and the compressed-gas-permeable swirl plate are preferably supplied with two separate compressed gas streams, which are sent to them in particular via the first compressed gas line and second compressed gas line already described above. The two separate compressed gas streams especially preferably have different volume flows, which are adjusted in particular through the at least one throttle element already described above.

These and other embodiments will be described below with reference to the following drawings.

DETAILED DESCRIPTION

Figure 1:
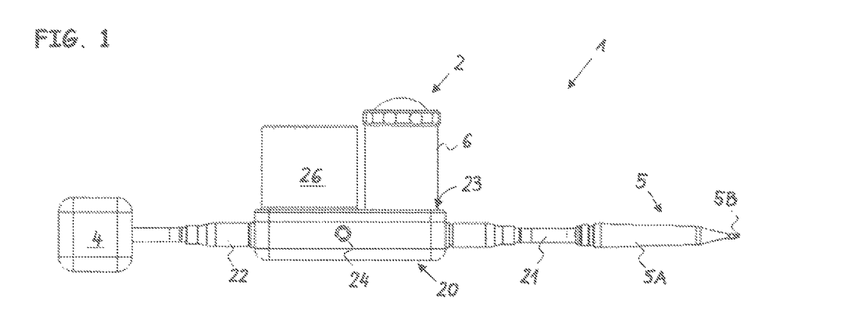
FIG. 1 shows a medical or dental device for dispensing a powdered medium.

The medical or dental device 1 shown in FIG. 1 for dispensing a powdered medium 30 to human or animal tissue or to a tissue replacement material comprises a container 2 for storing the powdered medium 30, a base part or operating part 20, a dispensing unit 5, a first supply tubing 21 which connects the base part or operating part 20 to the dispensing unit 5 and a second supply tubing 22 for connecting the base part or operating part 20 to a compressed gas source and/or a dental unit 4.

The compressed gas source is designed either as an independent element which is connected to the dental unit 4 or as part of the dental unit 4.

The dental unit 4 comprises, in addition to the compressed gas source or a connection thereto preferably a dental chair, a connection to a liquid source, a control device for controlling a plurality of different dental instruments, in particular a handpiece as well as a plurality of connections to which the dental instruments can be connected to receive media such as liquid (water), compressed gas, in particular compressed air and/or electricity from the dental unit 4. The medical or dental device 1 for dispensing a powdered medium 30 is preferably connectable to the dental unit 4 via one of these connections to receive at least compressed gas, optionally also water and/or electricity for operation of the medical or dental device 1.

The dispensing unit 5 comprises at least one nozzle device 5B for dispensing the powdered medium 30 in the direction of the human or animal tissue or the tissue replacement material. Preferably the dispensing unit 5 comprises a handle 5A which can be held by hand and on which the nozzle device 5B is attached. A line which conveys the compressed gas loaded with the powdered medium 30 is connected to the handle 5A and/or the nozzle device 5B and/or extends into the handle 5A and/or the nozzle device 5B.

The second supply tubing 22 comprises at least one line for conducting compressed gas from the compressed gas source and/or dental unit 4 to the base part or operating part 20 and/or in the direction of the dispensing unit 5. The first supply tubing 21 includes at least one line for conducting compressed gas loaded with the powdered medium 30 from the container 2 and/or the base part or the operating part 20 in the direction of the dispensing unit 5, in particular the nozzle device 5B. The first supply tubing 21 and/or the second supply tubing 22 preferably additionally comprise(s) a line for conducting a liquid in the direction of the dispensing unit 5 and/or an electrical line for conducting electricity to the base part or to the operating part 20 or in the direction of the dispensing unit 5.

The container 2 is provided on the base part or the operating part 20, for example, being detachably or undetachably connected thereto. A receptacle 23 for the container 2 and/or a connecting device for conducting compressed gas from the base part or the operating part 20 or from a compressed gas line arranged therein into the container 2 and/or from the container 2 into the base part or the operating part 20, or a compressed gas line arranged therein is/are preferably provided on the base part or the operating part 20.

In addition to the compressed gas lines and liquid lines already mentioned above, preferably also at least one adjusting element may be provided in the base part or the operating part 20, for example, at least one throttle element 18, 19 or 25 (see FIG. 2 or 3) in a compressed gas line or at least one valve for changing the flow rate of a liquid in a liquid line which conducts liquid in the direction of the dispensing unit 5. At least one operating element 24 with which a user can operate an adjusting element provided in the base part or the operating part 20 is preferably provided on the base part or the operating part 20, the adjusting element comprising for example, the valve mentioned above for varying the flow rate of a liquid or at least one throttle element mentioned above may be provided here.

A supply block 14 (FIG. 2), which connects the container 2 to the base part or operating part 20 and in particular to at least one of the compressed gas lines provided in the base part or operating part, is preferably also provided in the base part or operating part 20. The supply block 14, which is described in even greater detail below, is also designed for mechanical connection of the container 2 to the base part or operating part 20.

Figure 2:
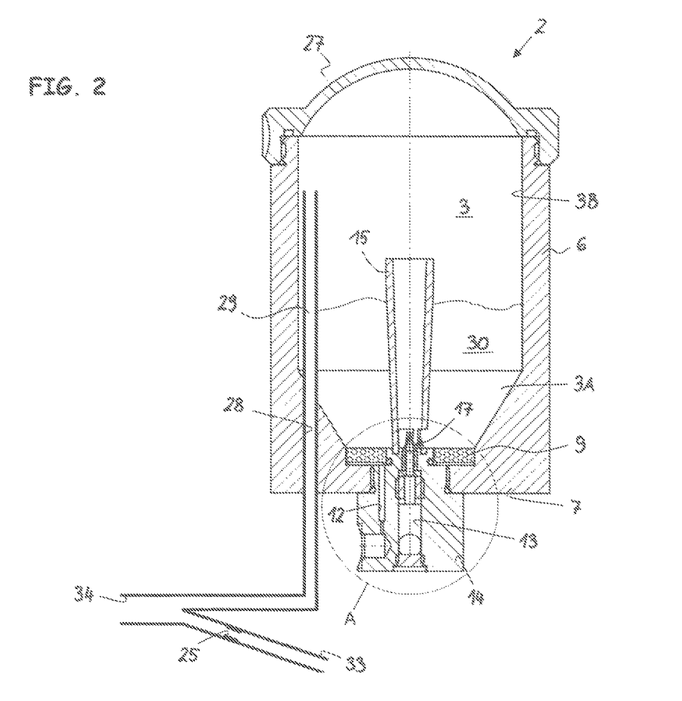
FIG. 2 shows a container for storing powdered medium that can be connected to the compressed gas source.

Finally, a moisture separator 26 for separating moisture out of the compressed gas, which is then sent to the container 2, is preferably arranged in the base part or the operating part 20. The moisture separator 26 includes, for example, filter material or a desiccant.

The container 2, which is shown enlarged in FIG. 2, includes a preferably cylindrical container wall 6, which defines at least a portion of a container interior space 3, a container bottom 7, connected to the container wall 6, and a container cover 27.

The container 2 can be connected by at least one connection to the compressed gas source 4 so that compressed gas from the compressed gas source 4 can be conducted into the container interior space 3. The container 2 can also be connected to the dispensing unit 5, so that the compressed gas that is loaded with the powdered medium 30 can be conveyed to the dispensing unit 5.

The container cover 27 is preferably arranged opposite the container bottom 7. The container cover 27 is preferably arranged movably or separably, preferably relative to the container 2, in particular the container wall 6, so that a powdered medium 30 can be filled into the container interior space 3. The container cover 27 preferably has a dome-type shape or a shape that is arched outward from the container interior space 3.

The container interior space 3 preferably comprises at least one cylindrical section 3B. Preferably a section 3A tapering in the direction of the container bottom 7 is connected to this cylindrical section 3B.

At least one bore 8 (see FIG. 3) through which compressed gas from the compressed gas source 4 can be conducted into the container interior space 3 is provided on the preferably circular container bottom 7. Another bore 28, through which the compressed gas loaded with the powdered medium 30 can exit from the container interior space 3, is preferably also provided on the container bottom 7. This hole 28 may also be provided at least partially or even completely in the container wall 6 and/or in the container cover 27.

A conveying tube 29 is preferably accommodated in the bore 28 or can be connected to it. The conveying tube 29 is designed to conduct the compressed gas loaded with the powdered medium 30 out of the container interior space 3, in particular in the direction of the dispensing unit 5. The conveying tube 29 is therefore in particular connected to a compressed gas line provided in the first supply tubing.

A compressed-gas-permeable swirl plate 9 made of a porous material is provided on the container bottom 7, wherein compressed gas can be conducted through the porous material into the container interior space 3 to loosen up or aerate at least a portion of the powdered medium 30 in the container interior space 3 without conveying the powdered medium 30 out of the container interior space 3 to the dispensing unit 5. The compressed-gas-permeable swirl plate 9 is preferably designed to be circular or a flat cylinder.

The height of the compressed-gas-permeable swirl plate 9 preferably amounts to several millimeters, for example, less than 7 mm, in particular less than 5 mm. The diameter of the compressed-gas-permeable swirl plate 9 is preferably less than 50 mm, in particular less than 35 mm. A plurality of channels or pores that open into openings on the top side 9A and on the bottom side 9B of the compressed-gas-permeable swirl plate 9 are provided in the body of the compressed-gas-permeable swirl plate 9 so that compressed gas can flow through the compressed-gas-permeable swirl plate 9.

The compressed-gas-permeable swirl plate 9 is arranged in particular adjacent to or in the section 3A of the container interior space 3 tapering in the direction of the container bottom 7 so that the powdered medium 30 in particular slides in the direction of or onto the compressed-gas-permeable swirl plate 9. The tapering section 3A especially preferably ends with its smallest diameter at the compressed-gas-permeable swirl plate 9, in particular on its top side 9A (see also FIG. 3), so that the (total) powdered medium 30 stored in the container interior space 3 is deposited directly on the compressed-gas-permeable swirl plate 9.

The compressed-gas-permeable swirl plate 9 is preferably fastened undetachably to the container 2, for example, being injected into the container 2, which is made of plastic.

As can be seen in FIG. 2 in particular, the compressed-gas-permeable swirl plate 9 forms an intermediate bottom which borders the container interior space 3 and separates the container interior space 3 and/or the powdered medium 30 from the container bottom 7. The compressed-gas-permeable swirl plate 9 or the intermediate bottom is preferably disposed in the container interior space 3 or adjacent to it, in particular in a receiving space having a cylindrical shape.

The compressed-gas-permeable swirl plate 9 additionally has a bore 11, preferably disposed centrally, so that compressed gas from the compressed gas source 4 can be conducted into the container interior space 3 (directly, without flowing through the porous material) in order to convey the powdered medium 30 out of the container interior space 3.

Figure 3:
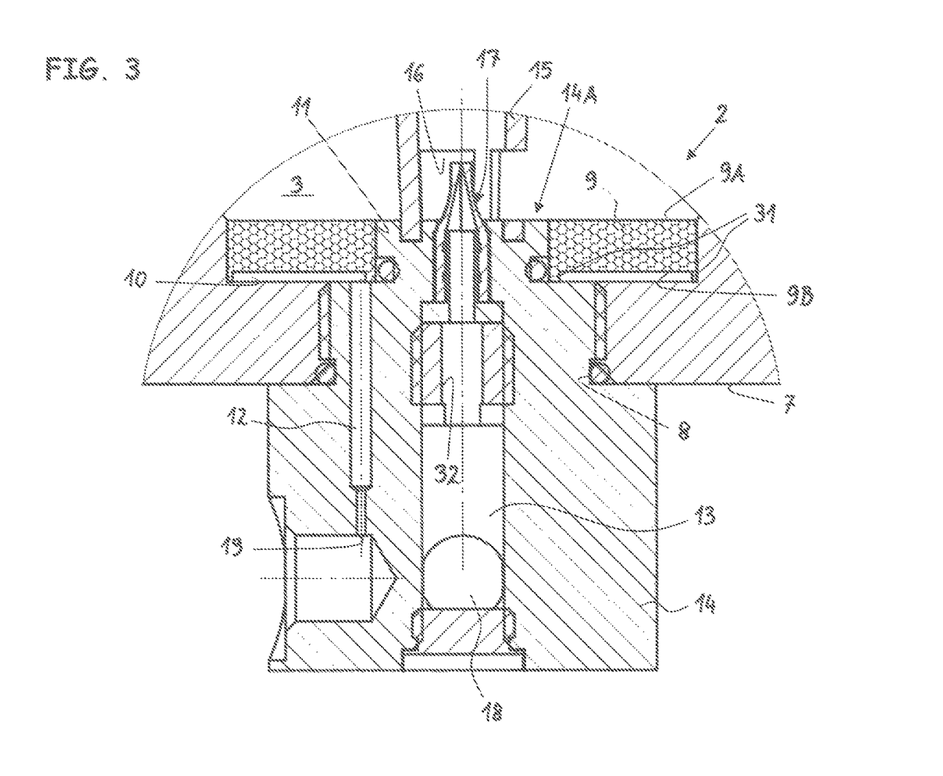
FIG. 3 shows the detail labeled as "A" in FIG. 2.

As can be seen in FIG. 3 in particular, the compressed-gas-permeable swirl plate 9 is spaced from the container bottom by at least one shoulder or a spacer 31, for example, by one spacer, or according to FIG. 3, two annular spacers. Therefore, a compressed gas chamber 10 extending over a large surface area along a bottom side 9B of the compressed-gas-permeable swirl plate 9 is formed beneath the compressed-gas-permeable swirl plate 9, in particular between the compressed-gas-permeable swirl plate 9 and the container bottom 7. This compressed gas chamber 10 is provided for planar supplying of compressed gas to the compressed-gas-permeable swirl plate 9.

The compressed gas chamber 10 is connected to the compressed gas source 4 via a first compressed gas line 12 so that compressed gas can be conveyed into the compressed gas chamber 10. The compressed gas spreads inside the compressed gas chamber 10 beneath the compressed-gas-permeable swirl plate 9, in particular beneath its bottom side 9B, and flows then through the porous material of the compressed-gas-permeable swirl plate 9 into the container interior space 3. The pressure drop in the compressed gas over the compressed-gas-permeable swirl plate and/or the volume flow of the compressed gas entering the compressed gas chamber 10 cause(s) the powdered medium 30 stored in the container interior space 3 to be loosened, aerated or fluidized by the compressed gas flowing through the compressed-gas-permeable swirl plate 9 without conveying any powdered medium 30 out of the container interior space 3 to the dispensing unit 5.

A second compressed gas line 13 conducts compressed gas directly into the container interior space 3 to convey the powdered medium 30 with the compressed gas out of the container interior space 3. To do so, the second compressed gas line 13 is also connected to the compressed gas source 4. The first compressed gas line 12 and the second compressed gas line 13 are preferably connected to the compressed gas source 4 via a common compressed gas line arranged in the second supply tubing 22. This common compressed gas line is preferably divided into the first compressed gas line 12 and the second compressed gas line 13 in the base part or the operating part 20, so that the two compressed gas lines 12, 13 are then formed as separate compressed gas lines.

The second compressed gas line 13 extends through the bore 11 in the compressed-gas-permeable swirl plate 9 and ends in or on the container interior space 3. A standpipe 15 is connected or attached to this end of the second compressed gas line 13.

The standpipe 15 extends further into the container interior space 3 up to a second free end, which is arranged above the powdered medium 30 in the container interior space 3. The standpipe 15 has a plurality of intake openings 16 for intake of powdered medium 30 stored in the container 2, so that powdered medium 30 is drawn through the compressed gas supplied by the second compressed gas line 13 through the at least one intake opening 16 into the standpipe 15 and conveyed with the compressed gas through the standpipe 15 in the direction of the second end.

On the second free end, the compressed gas together with the fluidized powdered medium 30 emerges from the standpipe 15 and flows through the container interior space 3 to the conveying tube 29, through which it leaves the container 2, as already described above.

The first compressed gas line 12 and the second compressed gas line 13 are arranged in a supply block 14 that can be connected to the container 2. The supply block 14 is formed as a connecting or attachment element between the container 2 and the base part or operating part 20. A plurality of sealing elements seal the supply block 14 with respect to the container 2, the container interior space 3, the compressed-gas-permeable swirl plate 9 and/or the compressed gas chamber 10.

The supply block 14 comprises an extension 14A on one end, in particular on the end facing the container interior space 3. This extension 14A protrudes into the bore 11 of the compressed-gas-permeable swirl plate and closes the bore 11 in particular. The extension 14A, preferably its top side facing the container interior space 3, thus in particular also forms a part of the aforementioned intermediate bottom together with the compressed-gas-permeable swirl plate 9.

A section of the second compressed gas line 13, which opens into an opening on the top side of the extension 14A, which opening is connected to the standpipe 15, is arranged in the extension 14A.

A non-return valve 17, designed to prevent powdered medium 30 to flow out of the container interior space 3 and into the compressed gas line 13, is arranged in the second compressed gas line 13, in particular in the supply block 14 or in its extension 14A. As shown in FIG. 3, the non-return valve 17 is supported on a shoulder formed by a constriction in the second compressed gas line 13 and affixed to said shoulder by a hollow screw 32 with an inside bore.

The first compressed gas line 12 and the second compressed gas line 13 each comprise a throttle element 18, 19, for example, a throttle valve so that the compressed gas volume flows that are flowing through the first compressed gas line 12 and the second compressed gas line 13 are adjustable independently of one another. In particular the two throttle elements 18, 19 are designed or can be operated, for example, with the operating element 24, such that the compressed gas volume flow that is flowing through the first compressed gas line 12 and the compressed gas volume flow that is flowing through the second compressed gas line 13 have different values. The compressed gas volume flow that flows through the first compressed gas line 12 is preferably greater than the compressed gas volume flow that flows through the second compressed gas line 13.

The medical or dental device 1 preferably includes another compressed gas line 33, which is designed to introduce pure compressed gas (without powdered medium 30) into the conveyor tube 29 or the compressed gas line 34 (see FIG. 2). Thereby it is possible to vary the concentration or amount of fluidized powdered medium 30 flowing in the direction of the dispensing unit 5, for example, by diluting the fluidized powdered medium 30 or by generating a back pressure in the conveying tube 29. Thus the delivery of an excess of powder in starting and stopping the device 1 in the direction of the handle 5A can also be prevented.

The compressed gas line 33 is connected to the compressed gas source 4 and receives compressed gas from this compressed gas source without containing any powdered medium 30. In addition, the compressed gas line 33 is connected to the conveyor tube 29 and/or to a compressed gas line 34 for conducting the fluidized powdered medium 30 in the direction of the dispensing unit 5, which is in turn connected to the conveyor tube 29, outside of the container 2, so that pure compressed gas can be conveyed into the conveyor tube 29 or into the compressed gas line 34.

In order to be able to vary the concentration or amount of fluidized powdered medium 30 flowing in the direction of the dispensing unit 5 particularly well, another throttle element 25 is provided in the compressed gas line 33. The throttle element 25 is in particular designed to be adjustable, for example, by means of an operating element 24 on the base part or the operating part 20.

The invention is not limited to the exemplary embodiments already described here but instead also includes all embodiments that use or contain the basic function principle of the invention according to the claims. In addition, each feature described or illustrated here can also be combined with any other feature described or illustrated here.

What is claimed is:

1. A medical or dental device for dispensing a powdered medium, comprising:

a container for storing the powdered medium in a container interior space, wherein the container can be connected to a compressed gas source, and compressed gas from the compressed gas source can be conducted into the container interior space to convey the powdered medium together with the compressed gas out of the container interior space, and wherein the container can be connected to a dispensing unit so that the powdered medium is conveyed with the compressed gas to the dispensing unit and can be dispensed by the dispensing unit in a desired direction, wherein the container comprises:

a container wall, which defines at least a portion of the container interior space, a container bottom that is connected to the container wall and has at least one bore through which compressed gas from the compressed gas source can be conducted into the container interior space, and a compressed-gas-permeable swirl plate made of a porous material which is provided at the container bottom, wherein compressed gas can be conducted through the porous material of the compressed-gas-permeable swirl plate into the container interior space to aerate at least a portion of the powdered medium in the container interior space without conveying the powdered medium out of the container interior space to the dispensing unit, wherein the compressed-gas-permeable swirl plate forms an intermediate bottom bordering the container interior space for storing the powdered medium and separating the container interior space from the container bottom.

2. The medical or dental device according to claim 1, wherein the compressed-gas-permeable swirl plate is arranged at or in a section of the container interior space tapering in the direction of the container bottom.

3. The medical or dental device according to claim 1, further comprising a compressed gas chamber for supplying compressed gas to the compressed-gas-permeable swirl plate to aerate at least a portion of the powdered medium in the container interior space, wherein the compressed gas chamber is arranged beneath the compressed-gas-permeable swirl plate and extends along a bottom side of the compressed-gas-permeable swirl plate.

4. The medical or dental device according to claim 3, further comprising a first compressed gas line which opens into the compressed gas chamber for supplying compressed gas to the compressed gas chamber.

5. The medical or dental device according to claim 4, further comprising a second compressed gas line for conducting compressed gas directly into the container interior space for conveying the powdered medium together with the compressed gas out of the container interior space.

6. The medical or dental device according to claim 5, wherein the second compressed gas line extends through a bore in the compressed-gas-permeable swirl plate.

7. The medical or dental device according to claim 5, further comprising a standpipe having a first end and a second end, wherein the standpipe extends into the container interior space, the first end is connected to the second compressed gas line and the standpipe comprises at least one intake opening for drawing in powdered medium stored in the container so that powdered medium is drawn by the compressed gas supplied by the second compressed gas line through the at least one intake opening into the standpipe and is conveyed with the compressed gas through the standpipe in the direction of the second end.

8. The medical or dental device according to claim 7, wherein the at least one intake opening is arranged on the first end of the standpipe close to the compressed-gas-permeable swirl plate.

9. The medical or dental device according to claim 1, wherein the compressed-gas-permeable swirl plate comprises a bore through which compressed gas from the compressed gas source can be conducted into the container interior space in order to convey the powdered medium out of the container interior space.

10. The medical or dental device according to claim 1, further comprising a supply block to which the container can be connected and which comprises at least one of a first compressed gas line for supplying compressed gas to the porous material of the compressed-gas-permeable swirl plate and a second compressed gas line for conducting compressed gas directly into the container interior space for conveying the powdered medium together with the compressed gas out of the container interior space.

11. The medical or dental device according to claim 10, wherein an extension of the supply block comprising a section of the second compressed gas line protrudes into a bore of the compressed-gas-permeable swirl plate through which compressed gas from the compressed gas source can be conducted into the container interior space in order to convey the powdered medium out of the container interior space.

12. The medical or dental device according to claim 1, further comprising a non-return valve which is designed to prevent powdered medium from flowing out of the container interior space into a compressed gas line for conducting compressed gas directly into the container interior space for conveying the powdered medium together with the compressed gas out of the container interior space.

13. The medical or dental device according to claim 1, further comprising a throttle element so that at least one of a volume flow of the compressed gas which can be conducted through the compressed-gas-permeable swirl plate and a volume flow of a compressed gas for conveying the powdered medium out of the container interior space to the dispensing unit is adjustable.

14. The medical or dental device according to claim 1, further comprising a dispensing unit having a nozzle arrangement which is designed for dispensing powdered medium in a direction of human or animal tissue or a tissue replacement material.

15. A medical or dental device for dispensing a powdered medium, comprising:

a container for storing the powdered medium in a container interior space, wherein the container can be connected to a compressed gas source, and compressed gas from the compressed gas source can be conducted into the container interior space to convey the powdered medium together with the compressed gas out of the container interior space, and wherein the container can be connected to a dispensing unit so that the powdered medium is conveyed with the compressed gas to the dispensing unit and can be dispensed by the dispensing unit in a desired direction, wherein the container comprises:

a container wall, which defines at least a portion of the container interior space, a container bottom that is connected to the container wall and has at least one bore through which compressed gas from the compressed gas source can be conducted into the container interior space, and a compressed-gas-permeable swirl plate made of a porous material which is provided at the container bottom, wherein compressed gas can be conducted through the porous material of the compressed-gas-permeable swirl plate into the container interior space to aerate at least a portion of the powdered medium in the container interior space without conveying the powdered medium out of the container interior space to the dispensing unit, wherein the compressed-gas-permeable swirl plate comprises a bore through which compressed gas from the compressed gas source can be conducted into the container interior space in order to convey the powdered medium out of the container interior space.

16. The medical or dental device according to claim 15, wherein the compressed-gas-permeable swirl plate is arranged at or in a section of the container interior space tapering in the direction of the container bottom.

17. The medical or dental device according to claim 15, wherein the compressed-gas-permeable swirl plate forms an intermediate bottom bordering the container interior space for storing the powdered medium.

18. The medical or dental device according to claim 15, further comprising a compressed gas chamber for supplying compressed gas to the compressed-gas-permeable swirl plate to aerate at least a portion of the powdered medium in the container interior space, wherein the compressed gas chamber is arranged beneath the compressed-gas-permeable swirl plate and extends along a bottom side of the compressed-gas-permeable swirl plate.

19. The medical or dental device according to claim 18, further comprising a first compressed gas line which opens into the compressed gas chamber for supplying compressed gas to the compressed gas chamber.

20. The medical or dental device according to claim 15, further comprising a second compressed gas line for conducting compressed gas directly into the container interior space for conveying the powdered medium together with the compressed gas out of the container interior space, wherein the second compressed gas line extends through or connects to the bore in the compressed-gas-permeable swirl plate.

21. The medical or dental device according to claim 20, further comprising a standpipe having a first end and a second end, wherein the standpipe extends into the container interior space, the first end is connected to the second compressed gas line and the standpipe comprises at least one intake opening for drawing in powdered medium stored in the container so that powdered medium is drawn by the compressed gas supplied by the second compressed gas line through the at least one intake opening into the standpipe and is conveyed with the compressed gas through the standpipe in the direction of the second end, wherein the at least one intake opening is arranged on the first end of the standpipe close to the compressed-gas-permeable swirl plate.

22. The medical or dental device according to claim 15, further comprising a supply block to which the container can be connected and which comprises at least one of a first compressed gas line for supplying compressed gas to the porous material of the compressed-gas-permeable swirl plate and a second compressed gas line for conducting compressed gas directly into the container interior space for conveying the powdered medium together with the compressed gas out of the container interior space.

23. The medical or dental device according to claim 15, further comprising a dispensing unit having a nozzle arrangement which is designed for dispensing powdered medium in a direction of human or animal tissue or a tissue replacement material.

24. A medical or dental device for dispensing a powdered medium, comprising:
a container for storing the powdered medium in a container interior space, wherein the container can be connected to a compressed gas source, and compressed gas from the compressed gas source can be conducted into the container interior space to convey the powdered medium together with the compressed gas out of the container interior space, and wherein the container can be connected to a dispensing unit so that the powdered medium is conveyed with the compressed gas to the dispensing unit and can be dispensed by the dispensing unit in a desired direction, wherein the container comprises:
a container wall, which defines at least a portion of the container interior space,
a container bottom that is connected to the container wall and has at least one bore through which compressed gas from the compressed gas source can be conducted into the container interior space,
a compressed-gas-permeable swirl plate made of a porous material which is provided at the container bottom, wherein compressed gas can be conducted through the porous material of the compressed-gas-permeable swirl plate into the container interior space to aerate at least a portion of the powdered medium in the container interior space without conveying the powdered medium out of the container interior space to the dispensing unit, and
a supply block to which the container can be connected and which comprises at least a compressed gas line for conducting compressed gas directly into the container interior space for conveying the powdered medium together with the compressed gas out of the container interior space, wherein
an extension of the supply block comprising a section of the compressed gas line protrudes into a bore of the compressed-gas-permeable swirl plate through which compressed gas from the compressed gas source can be conducted into the container interior space in order to convey the powdered medium out of the container interior space.

25. The medical or dental device according to claim 24, wherein the compressed-gas-permeable swirl plate is arranged at or in a section of the container interior space tapering in the direction of the container bottom.

26. The medical or dental device according to claim 24, wherein the compressed-gas-permeable swirl plate forms an intermediate bottom bordering the container interior space for storing the powdered medium.

27. The medical or dental device according to claim 24, further comprising a compressed gas chamber for supplying compressed gas to the compressed-gas-permeable swirl plate to aerate at least a portion of the powdered medium in the container interior space, wherein the compressed gas chamber is arranged beneath the compressed-gas-permeable swirl plate and extends along a bottom side of the compressed-gas-permeable swirl plate.

28. The medical or dental device according to claim 27, further comprising a compressed gas line which opens into the compressed gas chamber for supplying compressed gas to the compressed gas chamber.

29. The medical or dental device according to claim 24, further comprising a standpipe having a first end and a second end, wherein the standpipe extends into the container interior space, the first end is connected to the compressed gas line for conducting compressed gas directly into the container interior space and the standpipe comprises at least one intake opening for drawing in powdered medium stored in the container so that powdered medium is drawn by the compressed gas supplied by the compressed gas line for conducting compressed gas directly into the container interior space through the at least one intake opening into the standpipe and is conveyed with the compressed gas through the standpipe in the direction of the second end, wherein the at least one intake opening is arranged on the first end of the standpipe close to the compressed-gas-permeable swirl plate.

30. The medical or dental device according to claim 24, further comprising a dispensing unit having a nozzle arrangement which is designed for dispensing powdered medium in a direction of human or animal tissue or a tissue replacement material.

31. A medical or dental device for dispensing a powdered medium, comprising:
a container for storing the powdered medium in a container interior space, wherein the container can be connected to a compressed gas source, and compressed gas from the compressed gas source can be conducted into the container interior space to convey the powdered medium together with the compressed gas out of the container interior space, and wherein the container can be connected to a dispensing unit so that the powdered medium is conveyed with the compressed gas to the dispensing unit and can be dispensed by the dispensing unit in a desired direction, wherein the container comprises:
a container wall, which defines at least a portion of the container interior space,
a container bottom that is connected to the container wall and has at least one bore through which compressed gas from the compressed gas source can be conducted into the container interior space, and
a compressed-gas-permeable swirl plate made of a porous material which is provided at the container bottom, wherein compressed gas can be conducted through the porous material of the compressed-gas-permeable swirl plate into the container interior space to aerate at least a portion of the powdered medium in the container interior space without conveying the powdered medium out of the container interior space to the dispensing unit, wherein
the compressed-gas-permeable swirl plate extends from the container wall in a direction of a central longitudinal axis of the container to surround at least one of (i) a standpipe for conveying powdered medium stored in the container through the standpipe out of the container and (ii) a compressed gas line for conducting compressed gas directly into the container interior space for conveying the powdered medium together with the compressed gas out of the container interior space.

32. The medical or dental device according to claim 31, wherein the compressed-gas-permeable swirl plate is arranged at or in a section of the container interior space tapering in the direction of the container bottom.

33. The medical or dental device according to claim 31, wherein the compressed-gas-permeable swirl plate forms an intermediate bottom bordering the container interior space for storing the powdered medium.

34. The medical or dental device according to claim 31, further comprising a compressed gas chamber for supplying compressed gas to the compressed-gas-permeable swirl plate to aerate at least a portion of the powdered medium in the container interior space, wherein the compressed gas chamber is arranged beneath the compressed-gas-permeable swirl plate and extends along a bottom side of the compressed-gas-permeable swirl plate.

35. The medical or dental device according to claim 34, further comprising another compressed gas line which opens into the compressed gas chamber for supplying compressed gas to the compressed gas chamber.

36. The medical or dental device according to claim 31, wherein at least one of the standpipe extending into the container interior space and the compressed gas line for conducting compressed gas directly into the container interior space pass through or connect to a bore in the compressed-gas-permeable swirl plate.

37. The medical or dental device according to claim 31, further comprising a supply block to which the container can be connected and which comprises at least the compressed gas line for conducting compressed gas directly into the container interior space.

38. The medical or dental device according to claim 31, wherein the device comprises the standpipe and the compressed gas line for conducting compressed gas directly into the container interior space, wherein the standpipe comprises at least one intake opening for drawing in powdered medium stored in the container so that powdered medium is drawn by compressed gas supplied by the compressed gas line through the at least one intake opening into the standpipe and is conveyed with the compressed gas through the standpipe in the direction of a discharge end of the standpipe, wherein the at least one intake opening is arranged on an intake end of the standpipe close to the compressed-gas-permeable swirl plate.

39. The medical or dental device according to claim 31, further comprising a dispensing unit having a nozzle arrangement which is designed for dispensing powdered medium in a direction of human or animal tissue or a tissue replacement material.

40. The medical or dental device according to claim 31, wherein the compressed-gas-permeable swirl plate is formed circular or as a flat cylinder.

* * * * *